United States Patent [19]

Walter et al.

[11] 4,416,871

[45] Nov. 22, 1983

[54] INHIBITION BY PEPTIDES OF TOLERANCE TO AND PHYSICAL DEPENDENCE ON MORPHINE

[75] Inventors: Roderich W.Roderich Walter, Chicago, Ill., Mrs. Roderich W. Walter, Administrator; William A. Krivoy, Lexington, Ky.; Ronald F. Ritzmann, Chicago; Hemendra N. Bhargava, Wheaton, both of Ill.

[73] Assignee: The United States of America as represented by the Department of Health and Human Services, Washington, D.C.

[21] Appl. No.: 338,537

[22] Filed: Jan. 11, 1982

Related U.S. Application Data

[63] Continuation of Ser. No. 124,676, Feb. 26, 1980, abandoned, which is a continuation of Ser. No. 46,701, Jun. 8, 1979, abandoned, which is a continuation-in-part of Ser. No. 923,187, Jul. 10, 1978, abandoned.

[51] Int. Cl.³ .................... A61K 37/00; C07C 103/52
[52] U.S. Cl. ............................. 424/177; 260/112.5 R
[58] Field of Search ................. 424/177; 260/112.5 R

[56] References Cited

PUBLICATIONS

Chem. Abstr. vol. 90, (1979) 529n.
Pettit, "Synthetic Peptides" vol. I pp. 152, 153, 216 & 217.

*Primary Examiner*—Delbert R. Phillips
*Attorney, Agent, or Firm*—Holman & Stern

[57] ABSTRACT

Certain peptides administered during chronic morphine treatment were found to be effective in preventing development of tolerance and physical dependence. Particularly effective are prolyl-leucyl-glycinamide, cyclo(leucylglycine), and the protected peptide N-carbobenzoxy-prolyl-D-leucine, which, injected daily into mice receiving chronic morphine treatment, prevented the development of physical dependency as measured by changes in body temperature and body weight, either during abrupt or naloxone-induced withdrawal. But injection of peptide only on the last day of morphine treatment did not alter the overt signs of withdrawal. Daily injection of peptide was also effective in blocking the development of tolerance to analgesic and hypothermic effects of subsequent challenge doses of morphine. The peptide treatment did not alter the acute effects of morphine on either analgesia or body temperature. No effects on memory were noted, as evaluated in a one-trial passive avoidance task.

10 Claims, 2 Drawing Figures

INHIBITION BY PEPTIDES OF TOLERANCE TO AND PHYSICAL DEPENDENCE ON MORPHINE

GRANT INFORMATION

The described invention was developed in part under the following grants:
Illinois Department of Mental Health and Developmental Disabilities grant—904-02
U.S.P.H.S. grant—DA-02598
U.S.P.H.S. grant—AM-18399
N.I.A.A.A. grant—2696
N.S.F. grant—BNS 77-23306.

This is a continuation of application Ser. No. 124,676, filed Feb. 26, 1980 which in turn is a continuation of application Ser. No. 046,701 filed June 08, 1979, which is a continuation-in-part of application Ser. No. 923,187, filed July 10, 1978, all of which are now abandoned.

BACKGROUND OF THE INVENTION

This invention relates to novel compositions and to methods for inhibiting the development of tolerance to and dependence on drugs of the opioid type without substantial alteration of their analgesic effects. More particularly, the invention relates to compositions comprising opioid drugs and certain peptides and to administration of these compositions to obtain the desired inhibiting effect. In a specific aspect, the invention relates to pretreatment with certain peptides followed by daily administration of the peptide during chronic morphine treatment.

It is known that certain neurohypophyseal hormones, their analogs and disulfide-containing cyclic fragments of these hormones, facilitate development of physical dependence on and tolerance to actions of morphine (van Ree, J. M. and de Wied, D., *Life Sci.*, 19, 1331–1340[1976]). Several of these peptides, notably vasopressin and its analogs, can modify various aspects of behaviour including acquisition and extinction of conditioned responses in lower species as well as of memory in man. In addition, non-disulfide-containing linear hormone fragments, such as MSH-release inhibiting factor, prolyl-leucyl-glycylamide, N-carbobenzoxy-prolyl-leucyl-glycylamide, enzymatically stable cyclo(-leucyl-glycine), and prolyl-arginyl-glycylamide also exhibit these effects Walter, R., et al., *Proc. Natl. Acad. Sci. USA*, 72, 4180–4184[1975]).

Recently, in comparing the relative potencies of these peptides on facilitating the development of physical dependence on and tolerance to morphine it was found that not only oxytocin and 8-arginine vasotocin are more effective than 8-arginine vasopressin but that MSH-release inhibiting factor Pro-Leu-Gly-NH$_2$ and cyclo(Leu-Gly) are as effective as oxytocin in these tests (van Rec, J. M. and de Wied, D., *Life Sci.*, 19, 1331—1340[1976]).

BRIEF SUMMARY OF THE INVENTION

In accordance with this invention, it has surprisingly and unexpectedly been found that certain peptides containing selected aminoacid moieties inhibit rather than facilitate the development of tolerance to and physical dependence on opioid drugs. The effective peptides can be represented by the formula Z—Pro—A where Z represents a protecting group such as an N-carbobenzoxy group, and A represents an amino acid moiety selected from the group consisting of Leu, D-Leu, Met, βPhe, Gln, Ser, and Tyr.

Cyclic dipeptides having the lactam structure are also effective in the practice of this invention, particularly cyclo(leu-Gly) and cyclo(Pro-Phe).

Additional effective peptides can be represented by the formula

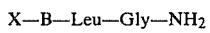

X—B—Leu—Gly—NH$_2$ where X is hydrogen or a protecting group such as an N-carbobenzoxy group, and B is selected from the group consisting of Pro and [Glu,(pyroglutaminyl)].

The term opioid drug as used herein includes the alkaloid drugs derived from opium such as morphine, heroin, and codeine. The above-identified peptides can be used effectively with these drugs, and more generally with opioid drigs as defined by W. K. Martin, Pharmacological Developments, 19, 463–552(1967) which citation is incorporated herein by reference.

The opioid drug and peptide can be administered by methods well known in the art. For example, pretreatment with the peptide is advantageously followed by daily administration of the peptide during drug treatment. The peptide and drug can also be administered sequentially, i.e. alternate administration of the peptide and drug. Further, the peptide and drug can be administered simultaneously. In the last-mentioned method of administration, a composition comprising the opioid drug and the peptide can be employed; the peptide comprises an amount sufficient to inhibit development of tolerance to and dependence on the drug.

DESCRIPTION OF THE PREFERRED EMBODIMENTS

Figure 1B:
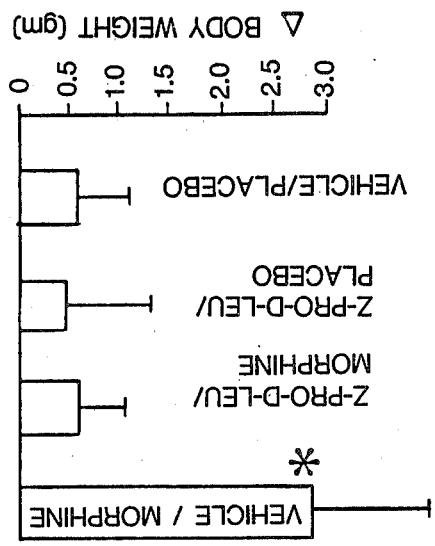
FIG. 1 illustrates the inhibition of development of physical dependence (abrupt withdrawal) by Z-Pro-D-Leu. Swiss Webster mice were implanted with either morphine or placebo tablets for a period of 3 days. Following removal of the pellets, body temperature and body weight were followed for 10 hours. Panel (a) represents the change in body temperature: (Δ—Δ) Z-Pro-D-Leu/morphine; (O—O) vehicle/morphine; (▲—▲) Z-Pro-D-Leu/placebo; (●—●) vehicle/placebo. Panel (b) represents the maximal loss in body weight during the same period.

The peptides utilized in the following experimental investigations were prepared by methods known in the art. For example, Z-Pro-D-Leu was prepared by the procedure of Schneider, et al., *J. Am. Chem. Soc.*, 84, 3006(1962). Suitable procedures are described in Synthetic Peptides, Van Nostrand Reinhold Company.

MATERIALS AND METHODS

Male C57B1/6J, Swiss Webster, and ICR mice weighing 26±4 g (SD) were used in these studies.

The mice were randomly divided into two groups. One received SC injections of water (vehicle) while the other received the peptide under investigation (50 μg/mouse on day one). Two hours later the mice were further subdivided and each subgroup was implanted with placebo or morphine pellets. The injections of vehicle and peptide were repeated 24 and 48 hours after the first injection in their respective groups. Morphine pellets containing 75 mg of morphine free base were implanted subcutaneously (SC) between 10-11 A.M. and were removed 3 days later at the same time. The control animals were implanted with placebo pellets. Body temperature and weight were measured daily at 11 A.M. Temperature was measured using a lubricated rectal probe inserted 2.5 cm into the rectum and measured with a telethermometer (Model 43TA Yellow Springs Instrument Co., Yellow Springs, Ohio).

The level of analgesia was tested on each of the three days of the experiment. This was accomplished by measuring the jump threshold to an increasing electrical current in an electrified grid attached to a BRS/LVE #SGS-004 shock generator/scrambler (Evans, W. D., *Phychopharmacol.*, 2, 318-325[1961]). Mice were tested only once and thereafter discarded from the experiment. When determining the effect of the peptide on overt signs of physical dependence (body temperature and weight) and tolerance (body temperature and analgesia), the peptide or vehicle was injected only once on the third day of the morphine or placebo pellet implantation (25 hours prior to the removal of the pellet).

To determine the effects of peptide treatment on the development of physical dependence, the abstinence syndrome was precipitated using the morphine antagonist naloxone (Endo Laboratories Inc., N.Y.) at the appropriate dose (0.1, 0.25, or 0.50 mg/kg) injected intraperitoneally (IP) one hour following removal of morphine and placebo pellets. Pellet removal was performed 24 hours after the last peptide injection. These mice were monitored for changes in body temperature (see above) and body weight at 15 min. intervals for one hour after the naloxone injection. Effects of removing the pellets (withdrawing morphine) were also assessed by utilizing body temperature and weight as physical dependence parameters; however, these measurements were made at 2 hour intervals for 10 hours after the removal of the pellets. Placebo implanted mice were treated in the same manner as the morphine pellet implanted mice.

Tolerance to hypothermic and analgesic effects of morphine injected intracerebroventricularly (ICV) was assessed 24 hours after the removal of the pellets in mice not injected with naloxone. The ICV injection was 40 μg of morphine sulfate solution in 10 μl volume. Body temperature was recorded prior to and at 10 and 15 min. after injection of morphine. Analgesia was determined one hour after the ICV injection.

Brain levels of morphine were measured in mice which received either the peptide or vehicle injections. For these studies mice were also sacrificed on the third day following morphine implantation. The mice were then sacrificed by decapitation, brains were rapidly removed, frozen on dry ice, and stored at −80° C. until assay for morphine content. Brain morphine concentrations were determined fluorometrically (Bhargava, H. N., *J. Pharma. Sci.*, 66, 1044-1045[1977]).

Statistical analysis unless otherwise noted for the above experiments was performed according to Winer (Winer, B. J., *Statistical Principles in Experimental Design* [McGraw-Hill, New York, N.Y.], p. 208, 1962) by the Student's t-test, and all data are expressed as means±standard deviations.

For behavioral studies using a one-trial passive avoidance task, male ICR, C57B1/6J, and Swiss Webster mice were used. The two-compartment passive avoidance box and details of the procedure have been described by Rainbow, T. C., et al., *Pharmaca. Biochem. Behav.*, 4, 347-349(1976). Five seconds after entering the large compartment, ICR mice received 0.4 mA of scrambled foot shock for 0.8 seconds; Swiss mice, 0.3 mA for 0.8 seconds; and C57B1/6J mice, 0.2 mA for 2 seconds. Several agents have been found to be amnesic under these conditions. Immediately after training mice were injected SC with 100 μg of peptide in saline or with saline alone. Mice were tested for retention 24 hours later. Mice that failed to enter the large compartment on testing within 180 seconds were removed and given a score of 180.

Effect of multiple injections of Z-Pro-D-Leu prior to and during the course of pellet implantation: On days 1 and 2 there was no significant difference in body temperature in either Swiss Webster or C57B1/6J mice comparing those receiving morphine with those receiving Z-Pro-D-Leu or vehicle; however, on the third day the morphine treated Swiss Webster mice which had been injected with Z-Pro-D-Leu had a statistically significant ($P<0.01$) lower body temperature ($X=-1.5°$ C., n=14) than the morphine-dependent mice injected with vehicle ($X=-0.5°$ C., n=18). Both groups displayed a biphasic response after morphine, with an initial hyperthermia on day one and a hypothermic response on subsequent days. Temperatures of placebo-implanted mice receiving either Z-Pro-D-Leu or vehicle did not change over the duration of pellet implantation. A similar relationship was found for the loss in body weight. Swiss Webster mice lost 16% and 14% in body weight when receiving Z-Pro-D-Leu or vehicle respectively. The C57B1/6J mice given Z-Pro-D-Leu/-morphine lost 14%, while the vehicle/morphine group lost 11% in body weight during this period regardless of peptide or vehicle injections. There was one significant strain difference, i.e. a greater mortality during morphine treatment of C57B1/6J mice (P=0.06, Binomial test). However, there was no difference in the number of deaths between strains when the group given peptide/morphine were compared with vehicle/morphine (C57B1/6J, P=0.32; Swiss Webster, P=0.65, Binomial test). No significant differences were observed in brain morphine levels on the third day of morphine treatment between Swiss Webster mice injected with Z-Pro-D-Leu (288±99 μg/g, n=6) and vehicle injected mice (310±28 μg/g, n=6).

*Inhibition of development of tolerance to and physical dependence upon morphine by Z-Pro-D-Leu.* The jump threshold in vehicle-injected, morphine-dependent mice decreased, indicating development of tolerance to the analgesic properties of morphine. Threshold scores were: 4.00±0.18; 3.50±0.52; 2.55±0.44; on days 1-3 respectively, (n=6 for each group). On the other hand, Z-Pro-D-Leu injected mice receiving morphine displayed no attenuation of the analgesic effects (day 1=4.07±0.27; day 2=4.27±0.62; day 3=4.45±0.64).

Figure 1A:
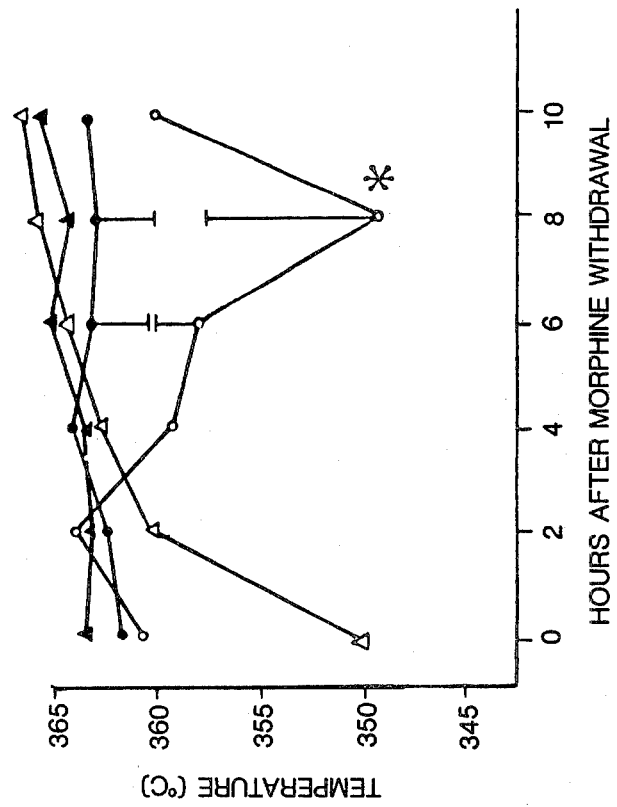

The effect of Z-Pro-D-Leu treatment on hypothermia and the loss of body weight during precipitated abstinence is presented in FIG. 1. There was a significant (P<0.001) difference between vehicle/morphine-treated and Z-Pro-D-Leu/morphine-treated mice at the time of maximum withdrawal, which occurs 8 hours after the removal of the pellets. There was no significant difference between the Z-Pro-D-Leu/morphine-treated mice and the two control groups at any of the time points on either of the variables.

Figure 2:
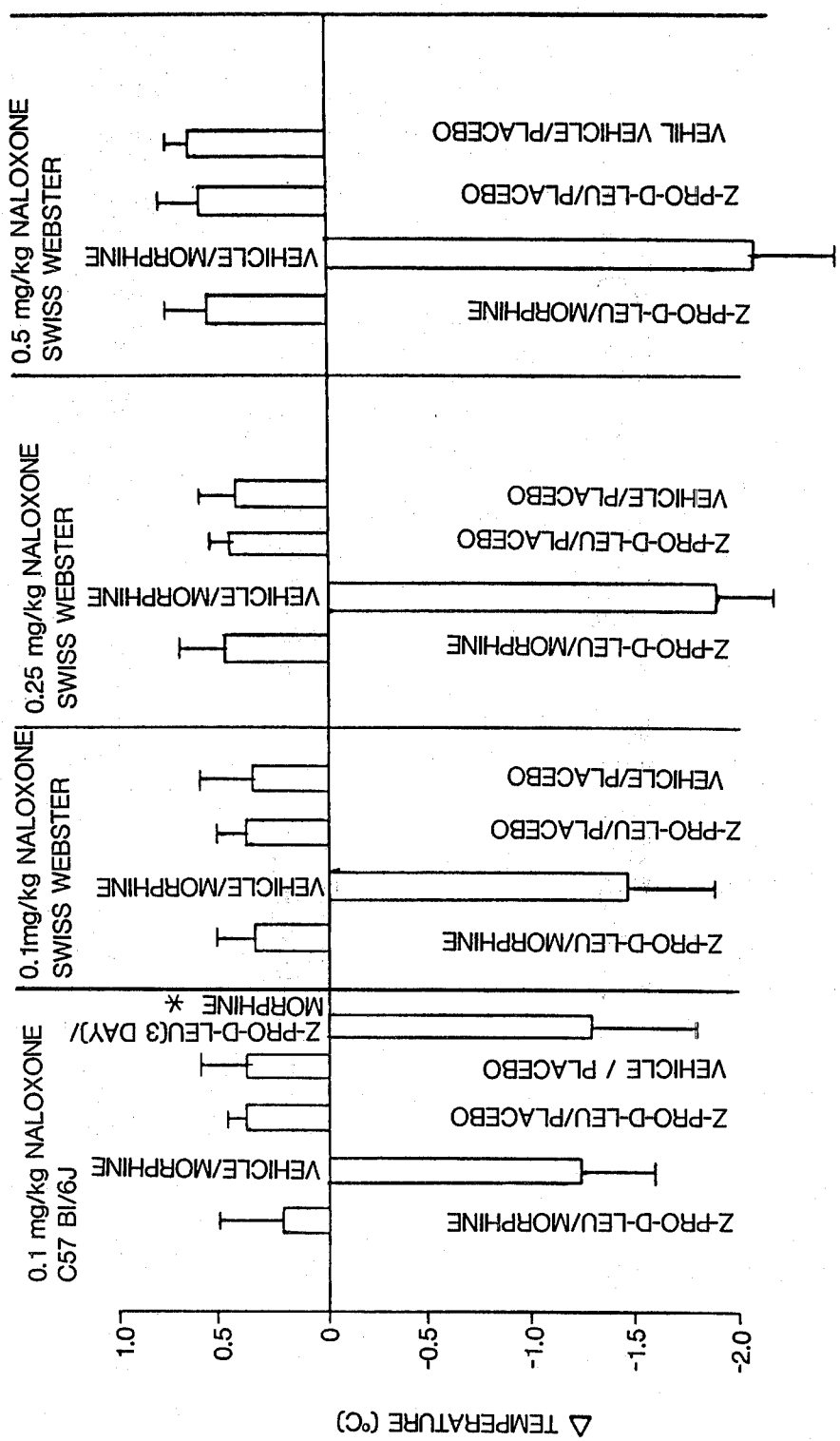
FIG. 2 illustrates the inhibition of the development of physical dependence (paloxone-precipitated withdrawal) by Z-Pro-D-leu. Particularly illustrated is the effect of increasing doses of naloxone on body temperature 30 min. post injection in various groups of two strains of mice one hour after the pellet removal. The asterisk refers to the appropriate control groups (vehicle/morphine, vehicle/placebo, and peptide/placebo) for single injection of Z-Pro-D-Leu given only on the third day of morphine treatment were tested; since these control groups did not differ from similar groups receiving multiple injections of peptide or vehicle, they are not shown.

Thirty minutes after injection of naloxone (0.1 mg/kg) in both strains of mice as well as doses of 0.25 or 0.50 mg/kg in the Swiss Webster mice, there was a significant hypothermia in vehicle/morphine-treated mice (FIG. 2). Maloxone injection into placebo implantd mice which had received either peptide or vehicle was followed by a mild hyperthermic response. Those mice which had received the Z-Pro-D-Leu/morphine treatment responded in a manner similar to mice which had no previous exposure to morphine by exhibiting a mild hyperthermia (see FIG. 2). On the other hand, mice which received the Z-Pro-D-Leu injection only on the third day responded as did the vehicle/morphine-treated mice, i.e. the injection of naloxone produced a hypothermic response in these animals which was not significantly different from that produced in the vehicle/morphine group (FIG. 2).

Morphine treated Swiss Webster mice given vehicle were tolerant to the hyperthermic (P<0.001) and analgesic (P<0.001) effects of the ICV injection of 40 g of morphine when compared to the vehicle placebo group (see Table I). This tolerance was evident for 24 hours after removal of the pellets.

TABLE I

Inhibition of Development of Tolerance to Morphine by Z-Pro—D-Leu in Mice[a]

| Group | $\Delta^t$ (10 min.) | $\Delta^t$ (15 min.) | Jump Threshold |
|---|---|---|---|
| C57B1/6J | | | |
| Control/ morphine (n = 9) | −0.73 ± 0.25* | −1.20 ± 0.47* | 2.06 ± 0.36** |
| Z-Pro—D-Leu/ morphine (n = 9) | −2.04 ± 0.42 | −2.12 ± 0.52 | 3.82 ± 42 |
| Z-Pro—D-Leu/ morphine (day 3 only; n = 6) | −0.75 ± 0.19* | −1.00 ± 0.16* | 2.12 ± 0.34** |
| Control/ placebo (n = 8) | −1.81 ± 0.27 | −1.94 ± 0.22 | 3.90 ± 0.68 |
| Z-Pro—D-Leu/ placebo (n = 8) | −1.76 ± 0.33 | −2.19 ± 0.41 | 3.79 ± 0.39 |
| Z-Pro—D-Leu/ placebo (n = 6; Day 3 only) Swiss Webster | −1.85 ± 0.25 | −1.88 ± 0.17 | 4.05 ± 0.85 |
| Control/ morphine (n = 8) | −0.53 ± 0.17* | −0.58 ± 0.24* | 2.65 ± 0.35** |
| Z-Pro—D-Leu/ morphine (n = 15) | −1.10 ± 0.29 | −1.32 ± 0.34 | 4.33 ± 0.54 |
| Control/ placebo (n = 8) | −1.18 ± 0.28 | −1.30 ± 0.48 | 4.25 ± 0.63 |
| Z-Pro—D-Leu/ placebo (n = 8) | −1.16 ± 0.30 | −1.48 ± 0.46 | 4.18 ± 0.41 |

[a]Mice were made morphine-dependent by SC implantation of 75 mg morphine pellets for a period of 3 days. Twenty-four hrs. following removal of the pellets the animals were challenged with an ICV injection of 40 g of morphine and body temperature measured 10 and 15 min. after the morphine injection. One hr. after the administration of morphine the jump threshold was determined. n equals number of animals. Level of significance (P <0.01 = *); (P <0.001 = **)

A similar diminished response after the ICV injection of 40 μg of morphine was found in C57B1/6J mice both for hypothermia (P<0.01) and for analgesia (P<0.001). Mice, which had been given Z-Pro-D-Leu during chronic morphine treatment responded to the ICV injection of morphine in a manner which was not significantly different from morphine-naive mice, but was significantly different from vehicle/morphine-treated mice (P<0.01). When the peptide was given only on the third day of pellet implantation,the mice responded similarly to those which had received the vehicle injection and morphine, i.e. giving the peptide after the development of tolerance to morphine did not effectively alter the manifestation of tolerance. It is also significant that there was no difference in the response to the challenge dose of morphine between the placebo-implanted mice which received the peptide in either strain and the placebo-implanted mice which received the vehicle injections (P<0.01).

Effects of treatment with Z-Pro-D-Leu on memory.

Effects of Z-Pro-D-Leu on memory of a one-trial passive avoidance task was tested in three strains of mice. For the ICR strain the median step-through latency value for peptide treated mice was 180±32.4 sec. (S.E.) (n=10; control 180±29.6, n=9). The respective values for Swiss Webster and C57B1/6J mice were 180±51.9, n=4 (control 180±17.5, n=10) and 180±0.0, n=4 (control 180±0.0, n=6) respectively, indicating that Z-Pro-D-Leu had no effect in retention of memory in any group.

In addition to Z-Pro-D-Leu, the peptides listed in Table II were evaluated for their ability to block development of physical dependence on morphine. The data indicate that the naturally occurring peptide Pro-Leu-Gly-NH$_2$ is highly effective. The addition of the protecting group N-carbobenzoxy (Z) did not alter the activity of the peptide in these tests, but addition of Z-Gly or substitution of [Glu (pyro-Glu) for the NH$_2$-terminal proline gave derivatives with reduced activity.

TABLE II

Effectivness of Peptides in Blocking Naloxone-precipitated Withdrawal in Mice(4)

| Treatment | n | Δt, °C.(1) | P(2) | Withdrawal, % of control(3) |
|---|---|---|---|---|
| Pro—Leu—Gly—NH$_2$(MIF) | 8 | +0.25 ± 0.24 | 0.001 | 0 |
| Δ$^3$Pro—Leu—Gly—NH$_2$ | 6 | −1.53 ± 0.81 | NS | 100 |
| Z-Pro—Leu—Gly—NH$_2$ | 6 | +0.07 ± 0.08 | 0.001 | 0 |

TABLE II-continued

Effectivness of Peptides in Blocking Naloxone-precipitated Withdrawal in Mice(4)

| Treatment | n | Δt, °C.(1) | P(2) | Withdrawal, % of control(3) |
|---|---|---|---|---|
| Z-Pro—Leu—Gly—N(CH$_3$)$_2$ | 6 | −0.47 ± 0.15 | NS | 100 |
| Z-Pro—Leu—Gly—COOH | 5 | −1.20 ± 0.39 | NS | 100 |
| Z-Gly—Pro—Leu—Gly—COOH | 9 | −0.07 ± 0.72 | 0.05 | 22 |
| [Glu—Leu—Gly—NH$_2$ | 9 | −0.27 ± 0.72 | 0.05 | 44 |
| Z-Leu—Gly—NH$_2$ | 13 | −0.75 ± 0.72 | NS | 70 |
| Pro—Leu | 8 | −0.13 ± 0.74 | 0.05 | 25 |
| Z-Pro—Leu—NH$_2$ | 5 | −0.95 ± 0.21 | NS | 100 |
| Z-Pro—Leu | 9 | +0.08 ± 0.93 | 0.05 | 22 |
| Z-D-Pro—D-Leu | 6 | +0.10 ± 0.56 | 0.01 | 0 |
| Z-D-Pro—Leu | 7 | +0.17 ± 0.71 | 0.01 | 14 |
| Z-Pro—D-Leu | 11 | −0.09 ± 0.58 | 0.01 | 9 |
| Z-Pro—Gly | 13 | −0.79 ± 0.78 | NS | 69 |
| Z-Pro—Ala | 6 | −0.74 ± 0.94 | NS | 63 |
| Z-Pro—D-Ala—DCHA | 9 | −0.55 ± 0.90 | NS | 50 |
| Z-Pro—Ile | 9 | −1.19 ± 0.91 | NS | 78 |
| Z-Pro—Val | 6 | −0.44 ± 0.48 | NS | 63 |
| Z-Pro—Glu | 11 | −0.63 ± 0.88 | NS | 45 |
| Z-Pro—Gln | 5 | +0.08 ± 0.33 | 0.01 | 0 |
| Z-Pro—Ser | 13 | −0.29 ± 0.73 | 0.05 | 39 |
| Z-Pro—Met | 6 | +0.17 ± 0.23 | 0.001 | 0 |
| Z-Pro—Phe | 9 | −1.03 ± 0.55 | NS | 89 |
| Z-Pro—ΔPhe | 9 | −0.36 ± 0.58 | 0.05 | 22 |
| Z-Pro—Tyr | 5 | +0.13 ± 0.31 | 0.01 | 0 |
| Z-Ala—Pro | 4 | −1.20 ± 0.21 | NS | 100 |
| Cyclo(Leu—Gly) | 14 | −0.02 ± 0.83 | 0.01 | 21 |
| Cyclo(Leu—Ala) | 5 | −1.80 ± 0.96 | NS | 100 |
| Cyclo(Pro—Phe) | 5 | −0.13 ± 0.55 | 0.05 | 20 |
| Cyclo(Pro—D-Leu) | 10 | −0.24 ± 1.06 | NS | 40 |
| Vehicle(control) | 33 | −1.18 ± 0.43 | — | 99 |

DCHA, dicyclohexylamine
(1)Difference in body temperature of the mouse determined just prior to naloxone injection (0.1 mg/kg) and 30 min. thereafter; values are expressed as mean ± SD.
(2)Means compared by Student's t test. P >0.05 was considered to be not significant (NS).
(3)Based on jumping, shakes, and diarrhea (animals showed 2 symptoms).
(4)Single dose of peptide = 50 μg per mouse was administered.

Replacement of the proline residue by 3,4-dehydroproline (Λ$^3$Pro), deletion of the proline moiety, dimethylation of the primary carboxamide group, or replacement of the glycinamide moiety by glycine resulted in inactive derivatives of MIF. However, the free dipeptide Pro-Leu exhibited activity, as did the four protected optical isomers: Z-Pro-Leu, Z-D-Pro-Leu, Z-Pro-D-Leu, and Z-D-Pro-D-Leu. Likewise the substitution of Gln, Met or Tyr for Leu in Z-Pro-Leu gave potent derivatives, but the substitution by either Ser or Phe gave peptides of reduced activity.

Another group of peptides that yielded active derivatives are the cyclic dipeptides possessing the lactam structure. Among those tested, cyclo(Leu-Gly) and cyclo(Pro-Phe) showed significant activity.

Dose-response experiments, shown in Table III, reveal MIF and cyclo(Leu-Gly) to be the most potent peptides tested in blocking physical dependence on morphine. MIF retained its effectiveness until doses of less than 0.5 μg per mouse were used; doses of either 0.05 or 0.005 μg per mouse failed to produce any alteration in the withdrawal response. Cyclo(Leu-Gly) was still effective in blocking physical dependence at a dose as low as 0.05 μg per mouse. Z-MIF, Z-Pro-Leu, and Z-Pro-D-Leu exhibited significant activities until a dose of less than 5 μg per mouse was administered.

It has been suggested that development of physical dependence upon certain central actions of morphine and other psychactive drugs is a manifestation of central nervous system(CNS) function analogous to memory or learning. Neurohypophyseal hormones as well as certain of their derivatives and fragments are known to alter memory, physical dependence on, and tolerance to morphine.

The instant invention, however, shows that certain peptides are effective in blocking development of tolerance to actions of morphine on pain threshold, body temperature, and weight. The blockade appears to last in excess of 24 hours.

TABLE III

Dose-response Effects of Peptides on Naloxone-precipitated Withdrawal

| Treatment | Dose, μg | n | Δt, °C. | P | Withdrawal, % of control |
|---|---|---|---|---|---|
| MIF | 50 | 8 | +0.25 ± 0.24 | 0.001 | 0 |
|  | 5 | 4 | +0.08 ± 0.28 | 0.001 | 0 |
|  | 0.5 | 5 | +0.18 ± 0.39 | 0.001 | 0 |
|  | 0.05 | 4 | −1.50 ± 0.14 | NS | 100 |
|  | 0.005 | 4 | −1.65 ± 0.17 | NS | 100 |
| Z-MIF | 50 | 6 | +0.07 ± 0.08 | 0.001 | 0 |
|  | 5 | 6 | −0.37 ± 0.26 | 0.05 | 33 |
|  | 0.5 | 6 | −0.65 ± 0.85 | NS | 66 |
| Z-Pro—Leu | 50 | 9 | +0.08 ± 0.93 | 0.01 | 18 |
|  | 5 | 4 | +0.33 ± 0.26 | 0.01 | 0 |
|  | 0.5 | 6 | −1.17 ± 0.17 | NS | 100 |
| Z-Pro—D-Leu | 50 | 11 | −0.09 ± 0.58 | 0.001 | 9 |
|  | 5 | 4 | −0.05 ± 0.37 | 0.01 | 25 |
|  | 0.5 | 6 | −1.47 ± 0.12 | NS | 100 |
| Cyclo(Leu—Gly) | 50 | 15 | −0.19 ± 0.58 | 0.001 | 18 |
|  | 5 | 5 | +0.47 ± 0.32 | 0.001 | 0 |
|  | 0.5 | 10 | +0.30 ± 0.29 | 0.001 | 0 |
|  | 0.05 | 10 | +0.27 ± 0.70 | 0.01 | 20 |
| Z-Pro—Phe | 50 | 9 | −1.03 ± 0.55 | NS | 99 |
|  | 5 | 5 | −0.69 ± 0.24 | NS | 100 |
|  | 0.5 | 6 | −0.69 ± 0.22 | NS | 100 |
|  | 0.05 | 4 | −1.60 ± 0.69 | NS | 100 |

TABLE III-continued

Dose-response Effects of Peptides on
Naloxone-precipitated Withdrawal

| Treatment | Dose, μg | n | Δt, °C. | P | Withdrawal, % of control |
|---|---|---|---|---|---|
| Vehicle | 0 | 33 | −1.18 ± 0.43 | — | 100 |

Table headings are the same as those in Table II.

Moreover, the peptides of this invention inhibit development of physical dependence, which accompanies chronic administration of morphine, since body weight and temperature of animals given both substances on a chronic basis did not alter during abstinence precipitated by naloxone or by withdrawal of the morphine.

The peptides of this invention can be administered during morphine treatment in amounts ranging from about 0.002 to about 100 mg/kg of body weight. The dosage will vary with the method of administration, with the particular species of animal treated, and with the activity of the peptide employed. With a dipeptide such as Z-Pro-D-Leu, a dosage in the range of about 0.20 to about 20 mg/kg can be employed advantageously; with a tripeptide such as Pro-Leu-Gly-NH$_2$, a dosage in the range of about 0.02 to about 20 mg/kg; and with a cyclic peptide such as cyclo(Leu-Gly), a dosage in the range of about 0.002 to about 20 mg/kg.

Because CNS studies on animals can in most cases be transferred to humans, the clinical implication of these results are clear. First is the possible use of the peptides of this invention in the control of patients on morphine with chronic pain without developing addiction liability. Second is the possible use of these peptides in treating a cycle of drug abuse. Moreover, it appears that these peptides have no undesirable effects on memory.

Although this invention has been disclosed in detail with particular reference to certain preferred embodiments thereof, it is understood that variations and modifications can be effected within the spirit and scope of the appended claims. It is intended that all material contained in the above description, tables, and figures shall be interpreted in an illustrative and not in a limiting sense.

What is claimed is:

1. An analgesic composition comprising morphine and a dipeptide selected from the group consisting of Pro-Leu, D-Pro-D-Leu, D-Pro-Leu, Pro-D-Leu, Pro-Gln, Pro-Ser, Pro-Met, Pro-ΔPhe, and Pro-Tyr, the dipeptide being present in amount sufficient to inhibit the development of tolerance to and physical dependence on the morphine without substantial alteration of its analgesic properties.

2. The composition of claim 1 wherein the primary amino function of the dipeptide is protected by the moiety selected from the group consisting of carbobenzoxy, t-butoxycarbonyl, α,α-dimethyl-3,4-dimethoxybenzyloxycarbonyl, triphenylmethyl, and benzyl.

3. An analgesic composition comprising morphine and a cyclic dipeptide selected from the group consisting of cyclo(Leu-Gly) and cyclo(Pro-Phe), the cyclic peptide being present in amount sufficient to inhibit the development of tolerance to and physical dependence on the morphine without substantial alteration of its analgesic properties.

4. An analgesic composition comprising morphine and a tripeptide amide selected from the group consisting of Pro-Leu-Gly-NH$_2$ and [Glu-Leu-Gly-NH$_2$,] the tripeptide amide being present in amount sufficient to inhibit the development of tolerance to and physical dependence on the morphine without substantial alteration of its analgesic properties.

5. The composition of claim 4 wherein the primary amino function of the tripeptide is protected by the moiety selected from the group consisting of carbobenzoxy, t-butoxycarbonyl, α,α-dimethyl-3,4-dimethoxybenzyloxycarbonyl, triphenylmethyl, and benzyl.

6. A method of inhibiting the development of tolerance to and physical dependence on morphine in mammals, without substantial alteration of the analgesic effects thereof, comprising the administration thereto, during morphine treatment, from about 0.20 to about 100 mg/kg of at least one of the peptides of claim 1.

7. The method of claim 6 wherein from about 0.20 to about 100 mg/kg of at least one of the protected peptides of claim 2 is utilized.

8. The method of claim 6 wherein from about 0.002 to about 100 mg/kg of at least one of the cyclic peptides of claim 3 is utilized.

9. The method of claim 6 wherein from about 0.02 to about 100 mg/kg of at least one of the peptides of claim 4 is utilized.

10. The method of claim 6 wherein from about 0.02 to about 100 mg/kg of at least one of the protected peptide-amides of claim 5 is utilized.

* * * * *